(12) United States Patent
Lapi et al.

(10) Patent No.: US 7,708,961 B2
(45) Date of Patent: May 4, 2010

(54) METHOD AND APPARATUS FOR ISOLATING THE RADIOISOTOPE $^{186}$RHENIUM

(75) Inventors: Suzanne Lapi, St. Louis, MO (US); Thomas J. Ruth, Vancouver (CA); Dirk W. Becker, Berlin (DE); John M. D'Auria, North Vancouver (CA)

(73) Assignee: Advanced Applied Physics Solutions, Inc., Vancouver, B.C. (CA)

( * ) Notice: Subject to any disclaimer, the term of this patent is extended or adjusted under 35 U.S.C. 154(b) by 0 days.

(21) Appl. No.: 12/078,409

(22) Filed: Mar. 31, 2008

(65) Prior Publication Data

US 2008/0241025 A1 Oct. 2, 2008

Related U.S. Application Data

(60) Provisional application No. 60/909,431, filed on Mar. 31, 2007.

(51) Int. Cl.
*C01G 45/00* (2006.01)
*C01G 47/00* (2006.01)
*C01G 57/00* (2006.01)
*C22B 47/00* (2006.01)
*C22B 61/00* (2006.01)
*G21G 1/06* (2006.01)

(52) U.S. Cl. .......................... 423/49; 376/158; 376/189
(58) Field of Classification Search ................. 420/434, 420/433; 423/49; 376/158, 189
See application file for complete search history.

(56) References Cited

U.S. PATENT DOCUMENTS

| 4,024,217 | A | | 5/1977 | Wexler et al. |
| 4,105,746 | A | | 8/1978 | Compton et al. |
| 5,204,530 | A | | 4/1993 | Chastagner |
| 5,862,193 | A | * | 1/1999 | Jia et al. ................... 376/158 |
| 2002/0114763 | A1 | * | 8/2002 | Glajch et al. ............. 424/1.11 |
| 2003/0228255 | A1 | * | 12/2003 | Park et al. ................ 424/1.49 |
| 2005/0008568 | A1 | * | 1/2005 | Mevellec et al. ......... 424/1.11 |

FOREIGN PATENT DOCUMENTS

| GB | 1385325 | 2/1975 |
| JP | 4071623 | 3/1992 |
| RU | 2158167 | 10/2000 |
| WO | WO 2005/077962 | 8/2005 |
| WO | WO 2006/074960 | 7/2006 |

OTHER PUBLICATIONS

Strem Chemicals, Inc., MSDS for potassium perrhenate.*
S. Lapi. Production and evaluation of high specific activity 186Re: an isotope for radioimmunotherapy in cancer treatment. PhD Dissertation, Simon Fraser University, 2007, 1-158.*
S. Lapi, W.J. Mills, J. Wilson, S. McQuarrie, J. Publicover, M. Schueller, D. Schyler, J.J. Ressler, T.J. Ruth. Production cross-section of 181-186Re isotopes from proton bombardment of natural tungsten, Appl. Radia. Isotop. 2007, 65, 345-349.*
S. Lapi and T.J. Ruth. Production of high specific activity 186Re, Abstracts of Papers, 228th ACS National Meeting, Philadelphia, PA, United States, Aug. 22-26, 2004, NUCL-026.*
V. Bechtold et al., "*Industrial Application of the Karlsruhe Compact Cyclotron*", Proc. $11^{th}$ Int. Conf. on Cyclotrons and their Applications, 1987, pp. 593-596.
Brown, "*Negative Ion Sources*", The Physics and Technology of Ion Source, Second Edition, 2004, pp. 285-311.
M.P. Dehnel et al., "*An ion source upgrade for an axial injection based commercial cyclotron*" Nuclear Instruments and Methods in Physics Research B 241, 2005, pp. 896-900.
K.G. Heumann, et al., "Recent Developments in Thermal Ionization Mass Spectrometric Techniques for Isotope Analysis," *Analyst*, vol. 120, pp. 1291-1299, 1995.
Written Opinion, Sep. 30, 2008 (copending Intl. Appl. No. PCT/IB2008/000761).
International Search Report, Sep. 30, 2008 (copending Intl. Appl. No. PCT/IB2008/000761.

* cited by examiner

*Primary Examiner*—Jerry Lorengo
*Assistant Examiner*—Carlos Barcena
(74) *Attorney, Agent, or Firm*—Harness, Dickey & Pierce, P.L.C.

(57) ABSTRACT

A method of isolating $^{186}$Re according to example embodiments may include vaporizing a source compound containing $^{185}$Re and $^{186}$Re. The vaporized source compound may be ionized to form negatively-charged molecules containing $^{185}$Re and $^{186}$Re. The negatively-charged molecules may be separated to isolate the negatively-charged molecules containing $^{186}$Re. The isolated negatively-charged molecules containing $^{186}$Re may be collected with a positively-charged collector. Accordingly, the isolated $^{186}$Re may be used to produce therapeutic and/or diagnostic radiopharmaceuticals having higher specific activity.

24 Claims, 5 Drawing Sheets

METHOD AND APPARATUS FOR ISOLATING THE RADIOISOTOPE $^{186}$RHENIUM

PRIORITY STATEMENT

This application claims the benefit under 35 U.S.C. § 119(e) of U.S. Provisional Application No. 60/909,431, filed on Mar. 31, 2007, the entire contents of which are incorporated herein by reference.

BACKGROUND

1. Technical Field

Example embodiments relate to the production and extraction of radioisotopes from a source compound.

2. Description of the Related Art

Therapeutic radiopharmaceuticals may be radiolabeled molecules used for delivering therapeutic doses of ionizing radiation with relatively high specificity to certain disease sites (e.g., cancerous tumors) in a patient's body. Additionally, recent research has been directed to the radiolabeling of monoclonal antibodies to evaluate the efficacy of radioimmunotherapy. A number of different radioisotopes have been used for these purposes, including $\alpha$, $\beta$, and auger electron emitters.

For those applications including site-specific therapy, it may be beneficial to use radiopharmaceuticals exhibiting higher specific activities. However, the presence of "cold" labeled antibodies may decrease the number of "hot" labeled antibodies that occupy the binding sites on the target cells. Consequently, reduced numbers of "hot" labeled antibodies may result in lower doses of ionizing radiation to the target cells, thus decreasing or impeding the ability of the treatment to induce the desired cell kill. Accordingly, higher specific radioactivity (SA) compounds may be beneficial to reduce the impact of "cold" labeled antibodies.

$^{186}$Re has been investigated as a candidate for radiotherapy, because $^{186}$Re decays by $\beta$-emissions and has a half-life of about 3.7 days. Additionally, $^{186}$Re exhibits a chemical similarity to $^{99m}$Tc, a radioisotope that has already been extensively studied and used in a variety of medical applications. $^{186}$Re may be produced in reactors via an $^{185}$Re(n, $\gamma$)$^{186}$Re reaction. Although radioimmunotherapy using $^{186}$Re has been successfully performed, higher SA $^{186}$Re compounds remain relatively difficult to obtain.

SUMMARY

A method of isolating a radioisotope for production of a higher specific activity radiopharmaceutical according to example embodiments may include vaporizing a source compound containing a first isotope and a second isotope, wherein the second isotope may be a radioisotope having therapeutic and/or diagnostic properties. The vaporized source compound may be ionized to form negatively-charged molecules containing the first isotope and the second isotope. The negatively-charged molecules may be separated by mass to isolate the negatively-charged molecules containing the second isotope. The isolated negatively-charged molecules containing the second isotope may be collected with a positively-charged collector.

A method of isolating $^{186}$Re according to example embodiments may include vaporizing a source compound containing $^{185}$Re and $^{186}$Re. The vaporized source compound may be ionized to form negatively-charged molecules containing $^{185}$Re and $^{186}$Re. An electric field may be generated to extract and accelerate the negatively-charged molecules away from the ion source. Additionally, a magnetic field may be generated to draw excess free electrons away from the negatively-charged molecules. The negatively-charged molecules may be separated by mass to isolate the negatively-charged molecules containing $^{186}$Re. The isolated negatively-charged molecules containing $^{186}$Re may be collected with a positively-charged collector.

BRIEF DESCRIPTION OF THE DRAWINGS

The features and advantages of example embodiments may become more apparent upon review of the detailed description in conjunction with the attached drawings.

DETAILED DESCRIPTION OF EXAMPLE EMBODIMENTS

It will be understood that when an element or layer is referred to as being "on", "connected to", "coupled to", or "covering" another element or layer, it may be directly on, connected to, coupled to, or covering the other element or layer or intervening elements or layers may be present. In contrast, when an element is referred to as being "directly on," "directly connected to" or "directly coupled to" another element or layer, there are no intervening elements or layers present. Like numbers refer to like elements throughout the specification. As used herein, the term "and/or" includes any and all combinations of one or more of the associated listed items.

It will be understood that, although the terms first, second, third, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of example embodiments.

Spatially relative terms, e.g., "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various embodiments only and is not intended to be limiting of example embodiments. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the shapes of regions illustrated herein but are to include deviations in shapes that result, for example, from manufacturing. For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of example embodiments.

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

Example embodiments relate to the production and isolation of anionic species from a source material. For instance, the methods according to example embodiments may be suitable for producing and isolating $^{186}$Re (rhenium-186) radioisotopes. As a result, higher specific radioactivity compounds containing the $^{186}$Re radioisotopes may be generated. The $^{186}$Re compounds may be utilized in a variety of medical applications. For example, an $^{186}$Re compound may be attached to one or more antibodies that are specific to the targeted receptors and utilized in radiation therapy and/or diagnostic procedures. The methods and apparatuses according to example embodiments may also be suitable for producing other higher specific radioactivity materials which may be utilized in a broader range of research, therapeutic, and/or diagnostic applications.

Conventional methods of producing $^{186}$Re may utilize $^{185}$Re (rhenium-185) or $^{186}$W (tungsten-186) as the starting material. The conventional method utilizing $^{185}$Re as the starting material may be represented by expression (1) below:

$$^{185}Re(n,\gamma)^{186}Re \qquad (1)$$

wherein the $^{185}$Re is converted to $^{186}$Re through neutron capture in a reactor. Although this method may have relatively high yield, separating the desired $^{186}$Re isotope from the source material may be difficult (e.g., via chemical separation), thus resulting in products exhibiting relatively low specific radioactivity.

The conventional method utilizing $^{186}$W as the starting material may be represented by expression (2) below:

$$^{186}W(p,n)^{186}Re \qquad (2)$$

wherein the $^{186}$W is converted to $^{186}$Re through a proton induced reaction within a particle accelerator. Although this method may have in a relatively low yield, separating the desired $^{186}$Re isotope from the source material may be easier (e.g., via chemical separation), thus resulting in products exhibiting improved levels of specific radioactivity.

However, because the cross-section for the $^{186}$W(p,n)$^{186}$Re reaction is relatively low, producing patient-dose quantities of $^{186}$Re in a cost effective manner using this method may not be feasible. Additionally, a relatively large number of curies of therapeutic and/or diagnostic radioisotopes may be required for clinical trials. Accordingly, an accelerator-based $^{186}$W production method may not even be able to produce the necessary quantities of therapeutic and/or diagnostic radioisotopes for a single patient per day (let alone thousands of patients yearly).

The methods and apparatuses according to example embodiments may involve the ionization and mass separation of $^{186}$Re from the $^{185}$Re starting material so as to facilitate the production of increased specific radioactivity $^{186}$Re compounds. The methods and apparatuses according to example embodiments may be able to achieve radioisotope production in the range of curies per day of material exhibiting relatively high specific radioactivity values (e.g. above 30 curies/mg).

As discussed above, conventional $^{186}$Re therapeutic and/or diagnostic compounds produced by neutron capture in a reactor may have relatively low specific radioactivity. Consequently, increases in the specific radioactivity of $^{186}$Re compounds according to example embodiments may be investigated to determine to the level of specific radioactivity required to improve therapeutic and/or diagnostic efficacy relative to that of conventional $^{186}$Re compounds. Once a target specific radioactivity has been established (e.g., the antibody-conjugated $^{186}$Re according to example embodiments exhibits improved efficacy over the conventional lower specific radioactivity $^{186}$Re while maintaining acceptable specificity so as to reduce or avoid impacting cells that do not express the target cell surface marker), methods and apparatuses according to example embodiments may be employed to produce usable quantities of the $^{186}$Re compound having the target specific radioactivity via ionization and mass separation of the $^{186}$Re radioisotope. The increased availability of $^{186}$Re compounds having higher specific radioactivity may facilitate further chemical developments and clinical studies directed to the use of $^{186}$Re-radiolabeled antibodies or small molecules.

Labeling an antibody with $^{186}$Re produced and recovered according to example embodiments may involve utilizing an activated ester as a bifunctional chelating agent (e.g., mercaptoacetyltriglycine (MAG3)). An example of a reaction scheme for the synthesis of the activated ester may be shown below by scheme (3).

Although $^{188}$Re may be available in no-carrier-added form via a $^{188}$W generator, $^{186}$Re may be the more suitable radioisotope, at least with regard to matching the physical decay properties of the radioisotope with the cell repair cycle. For example, the decay properties of $^{186}$Re may include a $\beta\text{-}_{Emax}$ of about 1 MeV and a $t_{1/2}$ of about 90 h, while the decay properties of $^{188}$Re may include a $\beta\text{-}_{Emax}$ of about 2 MeV and a $t_{1/2}$ of about 17 h. Thus, the decay properties of $^{186}$Re may be more suited for the radioisotope therapy of small tumors. Additionally, generation of the $^{188}$W precursor (for $^{188}$Re production) involves a double neutron capture reaction which can be achieved at only a few reactors worldwide, while facilities capable of the $^{185}$Re(n,γ)$^{186}$Re reaction are much more widely available. According to example embodiments, higher specific radioactivity $^{186}$Re compounds may be generated with greater ease from the $^{185}$Re(n,γ)$^{186}$Re reaction product. Furthermore, $^{186}$Re compounds according to example embodiments may exhibit improved physical properties with regard to energy and half-life relative to $^{90}$Y and $^{131}$I, respectively, wherein $^{90}$Y and $^{131}$I are commonly used radioisotopes.

The methods and apparatuses according to example embodiments relate to the production of increased specific radioactivity $^{186}$Re compounds. Additionally, the specific radioactivity of the $^{186}$Re compounds may be adjusted via the inclusion of natural rhenium so as to achieve a level of specific radioactivity that exhibits the desired balance of therapeutic and/or diagnostic efficacy and value. As discussed above, $^{186}$Re may be a suitable candidate for radiotherapy, because its decay properties include β-emissions and a half-life of about 3.7 days. Furthermore, $^{186}$Re has a chemical similarity to $^{99m}$Tc, which has already been extensively studied. However, although production facilities capable of producing $^{186}$Re via the $^{185}$Re(n,γ)$^{186}$Re reaction may be readily available, the conventional $^{185}$Re(n,γ)$^{186}$Re reaction method typically results in a $^{186}$Re product exhibiting relatively low specific radioactivity which limits its utility in therapeutic and/or diagnostic applications involving site-specific targets.

To improve the production of higher specific radioactivity $^{186}$Re compounds, methods and apparatuses according to example embodiments may employ a cusp ion source to ionize and extract the $^{186}$Re radioisotopes from the starting material. Additional information regarding cusp ion source technology may be found, for example, in Dehnel, et al., NIM B, vol. 241, pp. 896-900, 2005, the entire contents of which are incorporated herein by reference.

Figure 1:
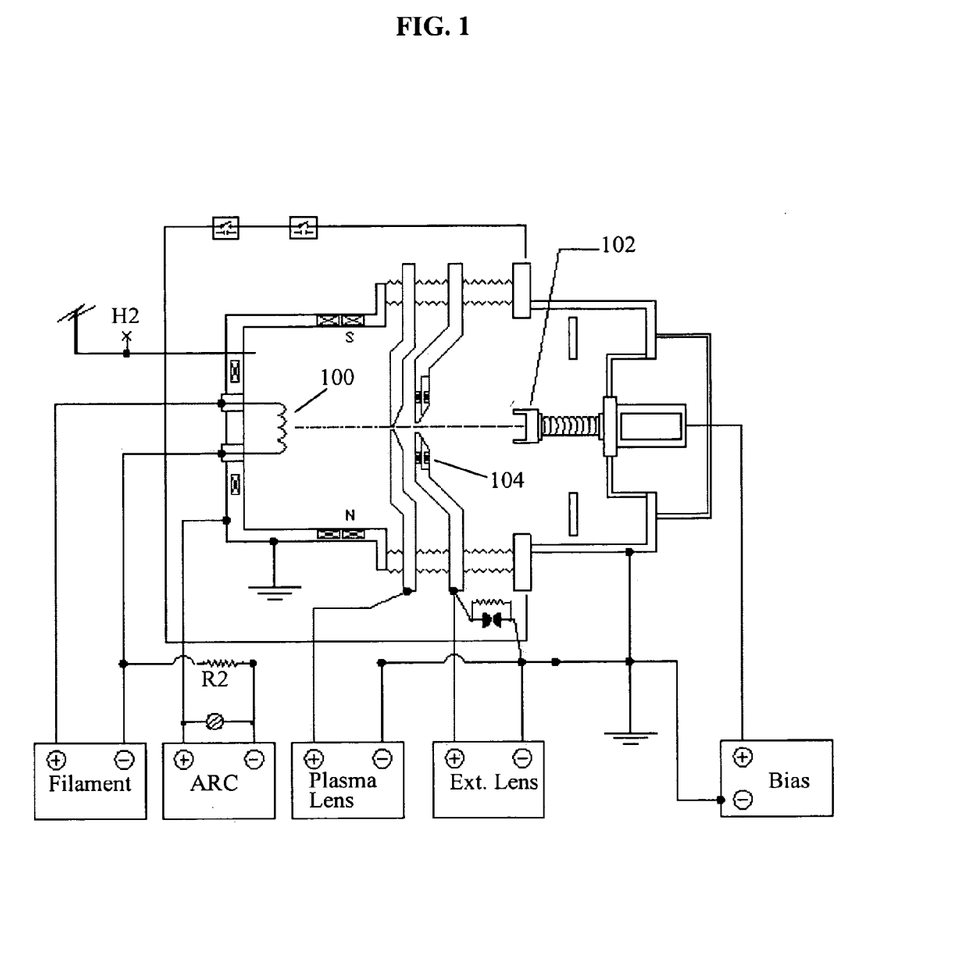
FIG. 1 is an electrical schematic diagram of a rhenium ion source according to example embodiments.

FIG. 1 is an electrical schematic diagram of a rhenium ion source according to example embodiments. Referring to FIG. 1, plasma may be generated by electron emission from the filament 100 at a current of about 130 Amps. The plasma may be maintained in a stable state by the addition of hydrogen ($H_2$) gas. As a result, the majority of the ions implanted into the Faraday cup 102 may be H$^-$ ions. The extraction lens 104 (e.g., 2 kV) and Faraday cup 102 (e.g., 20 kV Bias) may be maintained at a positive voltage so as to extract negative ions from the source. It should be understood that the rhenium ion source according to example embodiments is not limited to the parameters set forth in FIG. 1. Rather, one of ordinary skill in the art will readily appreciate that, in view of the present disclosure, other variations are possible.

Figure 2:
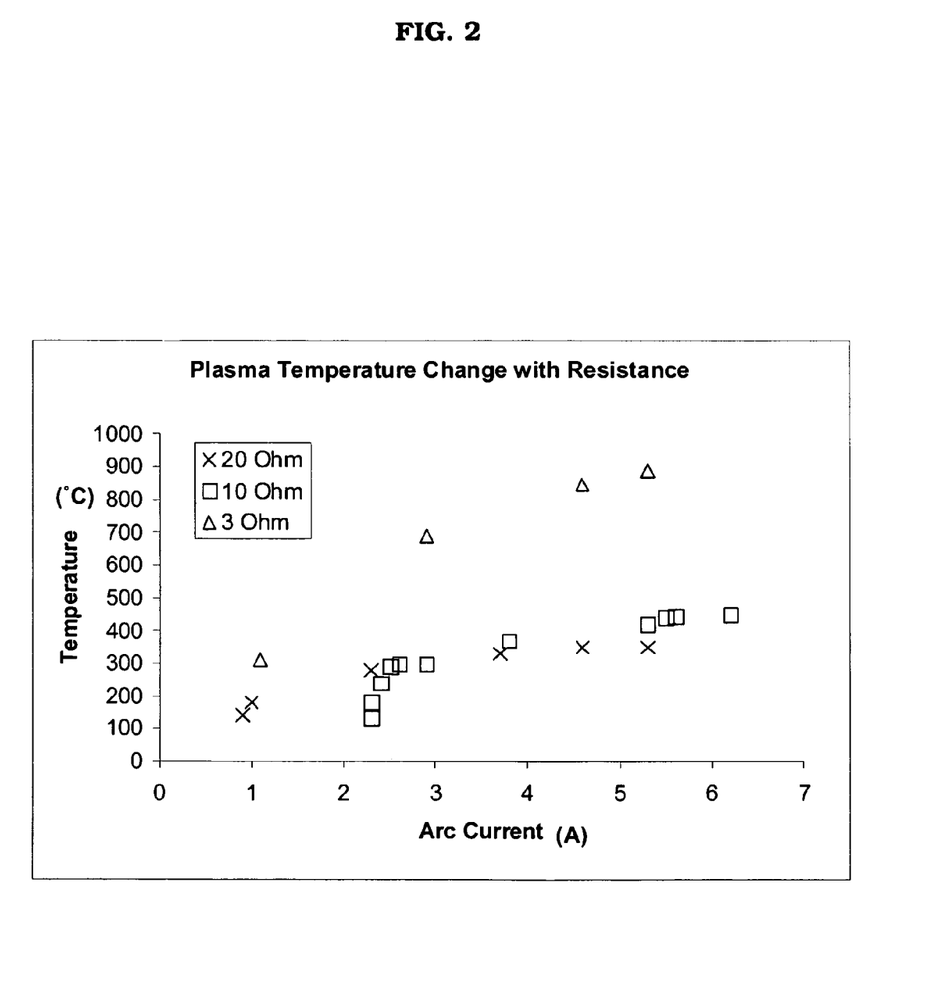
FIG. 2 is a graph showing plasma temperature change with resistance according to example embodiments.

Using the example discussed above, initial tests may be conducted to determine the temperature of the plasma as a function of the resistance of resistor R2. As the filament current is increased, the arc across the plasma may also increase. The resistor R2 may limit the feedback between these two power supplies, so it may be beneficial to determine the highest resistance of the resistor R2 that will allow the maintenance a temperature that is sufficiently high to keep a rhenium oxide species volatile. A graph of this plasma temperature change with resistance is shown in FIG. 2. In light of the results shown in FIG. 2, the R2 resistor value may be maintained at about three ohms to ensure adequate vaporization. However, in view of the present disclosure, those of ordinary skill in the art will readily appreciate that a variety of circuits and apparatuses may be used to achieve the target plasma heating and that such modifications would not detract from the fundamental operation of the disclosed device.

In a method according to example embodiments, H$^{188}$ReO$_4$ was utilized as the radioisotope source compound. The H$^{188}$ReO$_4$ was collected on a quartz dish, dried, and placed in the ion source chamber. The pressure in the ion source chamber was reduced to below atmospheric pressure, and hydrogen plasma was produced within the ion source chamber. Consequently, the plasma heated the radioisotope source compound to a temperature sufficient to induce vaporization of the source compound. As the molecules of the source compound vaporized and interacted with the plasma (e.g., H$^-$ ions), negatively charged species were produced and accelerated toward the collector assembly. In this instance, the collector assembly was a Faraday cup, although example embodiments are not limited thereto.

Without being bound by theory, it is believed that the H$^-$ plasma interacts with the radioisotope source compound to produce one or more negatively charged ions (e.g., $ReO_n^-$) which are accelerated toward and collected in the Faraday cup. As will be appreciated by those ordinarily skilled in the art, this technique may also be applicable to other radioisotope source compounds (e.g., oxides, nitrides, carbides) which can be vaporized under the appropriate temperature and pressure combination maintained within the ion source chamber. Similarly, those ordinarily skilled in the art will also appreciate that the proper temperature and pressure may be a function of the materials utilized, the power applied, and the configuration of the source chamber and the ancillary equipment (e.g., gas mass flow controllers, valving, control systems, vacuum pumps, cooling assemblies).

The ion source chamber according to example embodiments may be constructed and operated so as to enable the creation and maintenance of the appropriate temperature and pressure conditions within the ion source chamber. As a result, the radioisotope source material may be vaporized at a suitable rate without damaging the ion source chamber or generating undesirable levels of byproducts that would interfere with the collection and enrichment of the targeted radioisotope. For example, the radioisotope source compound utilized in the ion source may exhibit satisfactory vaporization at temperatures below about 1300° C. Additionally, it may be beneficial for the radioisotope source compound to exhibit satisfactory vaporization at temperatures below about 900° C. so as to allow for the utilization of a wider range of materials in the construction of the ion source chamber. Furthermore, it may be beneficial for the radioisotope source compound utilized in the ion source to exhibit satisfactory vaporization at pressures below about 1 Torr.

As discussed above, the use of an appropriately sized R2 resistor according to example embodiments may allow the production of plasma capable of heating the source compound and its vessel to temperatures in excess of about 500° C., thereby volatilizing the rhenium oxide. Consequently, the source compound may dissociate within the plasma, with the resulting fragments becoming negatively charged ions (e.g., $ReO_n^-$). The negatively charged ions may be extracted from the ion source chamber and implanted on the Faraday cup.

After an implant cycle, the Faraday cup may be removed and evaluated using gamma spectroscopy to determine the amount of radioactivity implanted in the Faraday cup. Ion source performance analysis indicates that the apparatus illustrated in FIG. 1 may achieve implant beam currents of about 1.2 mA (with $H^-$ constituting a major portion of the beam and the radioisotope source compound species $ReO_n^-$ constituting a minor portion of the beam).

Figure 3:
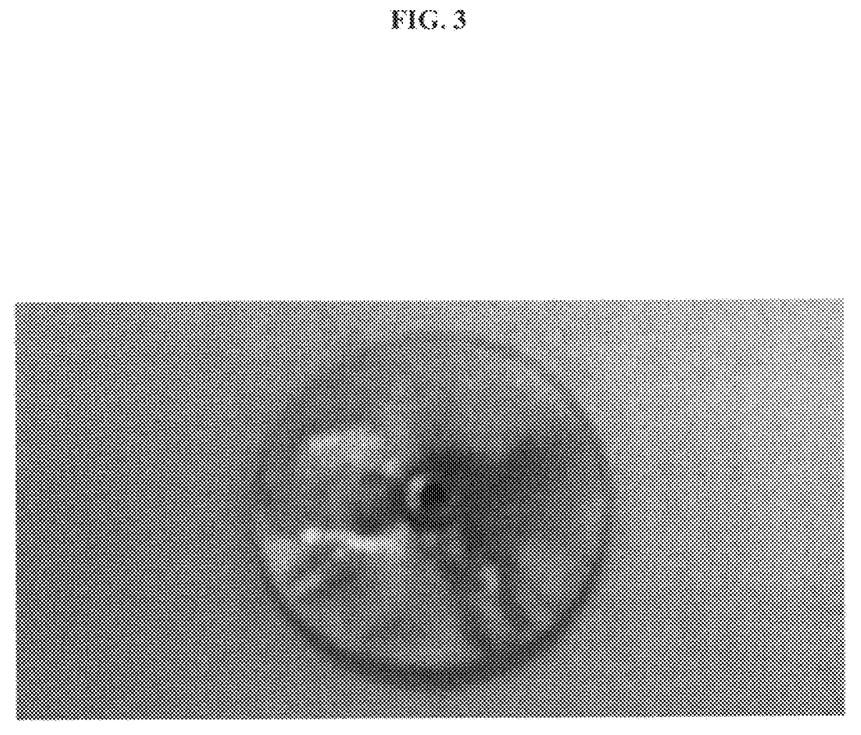
FIG. 3 is a photographic image of a Faraday cup (post implant) according to example embodiments.

FIG. 3 is a photographic image of a Faraday cup after one hour of irradiation with the extracted Re beam according to example embodiments. Because the power of the accelerated beam exceeded the tolerance of the Faraday cup based on its initial configuration, the Faraday cup became discolored and deformed, as shown in FIG. 3. When the Faraday cup and the source compound container from the ion source chamber were analyzed with a high purity Germanium detector for radioactivity, the initial results indicated that approximately 20% of the radioactivity that was volatilized from the source was actually implanted in the Faraday cup.

Additional efforts may be directed toward improving the extraction percentage, wherein the extraction percentage may be the portion of the desired rhenium radioisotopes released from the source compound vessel (e.g., quartz dish). For example, by providing a combination of both stable and radioactive rhenium atoms on the source compound vessel used in the ion source chamber, the majority of the radioisotope atoms may be successfully vaporized, ionized, and collected at the target assembly (e.g., a Faraday cup). As will be appreciated by those ordinarily skilled in the art, various combinations of stable and radioactive rhenium atoms and extraction voltages may provide for further improvements in the extraction percentage.

Figure 4:
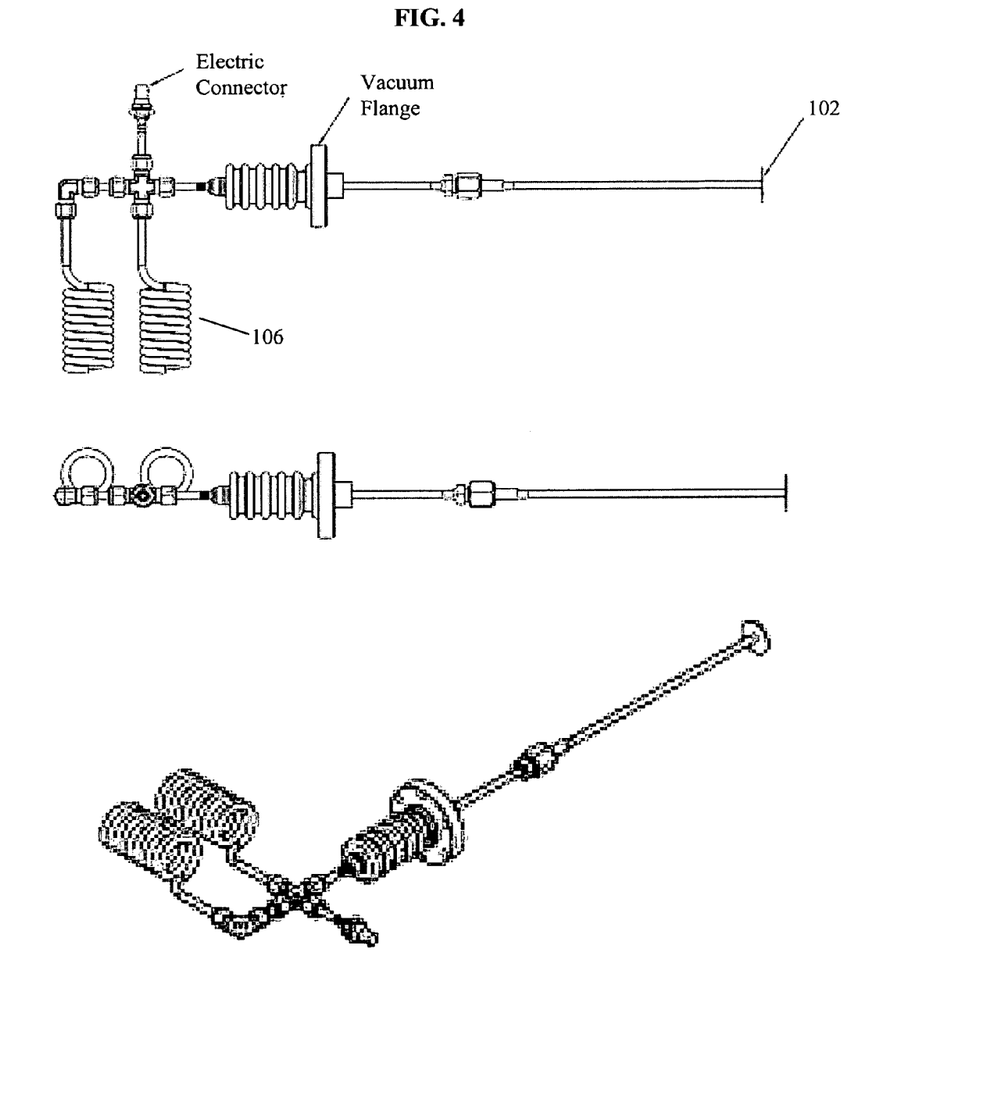
FIG. 4 is a plan view, side view, and perspective view of a water-cooled Faraday cup for a rhenium ion source according to example embodiments.

FIG. 4 is a plan view, side view, and perspective view of a water-cooled Faraday cup for a rhenium ion source according to example embodiments. A modified apparatus incorporating a water-cooling arrangement 106 for the Faraday cup 102 may reduce the damage suffered by the Faraday cup 102 during implantation. For example, the water-cooled Faraday cup 102 may be beneficial during prolonged implants and may increase the removability of the radioactivity from the source.

The methods and apparatuses according to example embodiments may facilitate the production of useful quantities of increased specific radioactivity $^{186}$Re and related compounds. For example, a $^{186}$Re source compound may be placed in an ion source chamber and exposed to a temperature and pressure combination that is sufficient to induce the vaporization of the source compound. Hydrogen plasma may be utilized to both heat the source compound and to ionize the resulting molecular fragments to produce Re-containing anions. The Re-containing anions may be extracted from the ion source chamber and collected in a positively-charged target vessel.

As will be appreciated by those ordinarily skilled in the art, alternative configurations may provide for supplemental heating sources. For example, resistance heating and/or microwave heating may be used in lieu of or in addition to the plasma for vaporizing the source compound. Similarly, alternative structures (e.g., higher voltage filaments) may be utilized for imparting a negative charge to the vaporized source compound fragments so that the desired species (e.g., radioactive species) may be extracted from the ion source chamber and accelerated toward a collection assembly. Furthermore, the source compound may be introduced into the ion source chamber as a vapor (e.g., perrhenic acid). Thus, when properly configured according to the present disclosure, various alternative example embodiments may be attained for purposes of producing higher specific radioactivity compounds. Depending on the separation assembly (e.g., magnetic separation assembly), specific radioactivity values in the range of 30 curies/mg to over 300 curies/mg may be achieved using the methods and apparatuses according to example embodiments.

As discussed above, a CUSP ion source may be used to separate $^{186}$Re from neutron-irradiated $^{185}$Re by ionizing perrhenate molecules and implanting them on a water-cooled Faraday cup. The CUSP ion source may provide satisfactory results even when the perrhenate ion beam is not controlled and is contaminated with a relatively high current negative ion hydrogen beam.

Alternatively, a negative ion surface thermal ionization (NIST) process may be utilized to ionize the perrhenate molecules. Depending on the circumstances, negative ion surface thermal ionization may be more efficient and effective than CUSP ionization. Methods and apparatuses according to example embodiments with regard to negative surface ionization are described below. Furthermore, additional information relating to surface ionization may be found in Brown, Ian G. (Ed.), "The Physics and Technology of Ion Sources," $2^{nd}$ edition, Wiley-VCH, Weinheim, 2004, the entire contents of which are incorporated herein by reference.

When a neutral atom or molecule impinges upon and is temporarily adsorbed by a heated surface during a negative ion surface thermal ionization (NIST) process, the heated surface may be hot enough to prevent the atoms from remaining adsorbed. As a result, the atoms or molecules may be ionized when leaving the heated surface. A negative ion may be produced when the work function (Φ) of the heated surface is smaller than the electron affinity (EA) of the atom or molecule impacting the heated surface.

Figure 5:
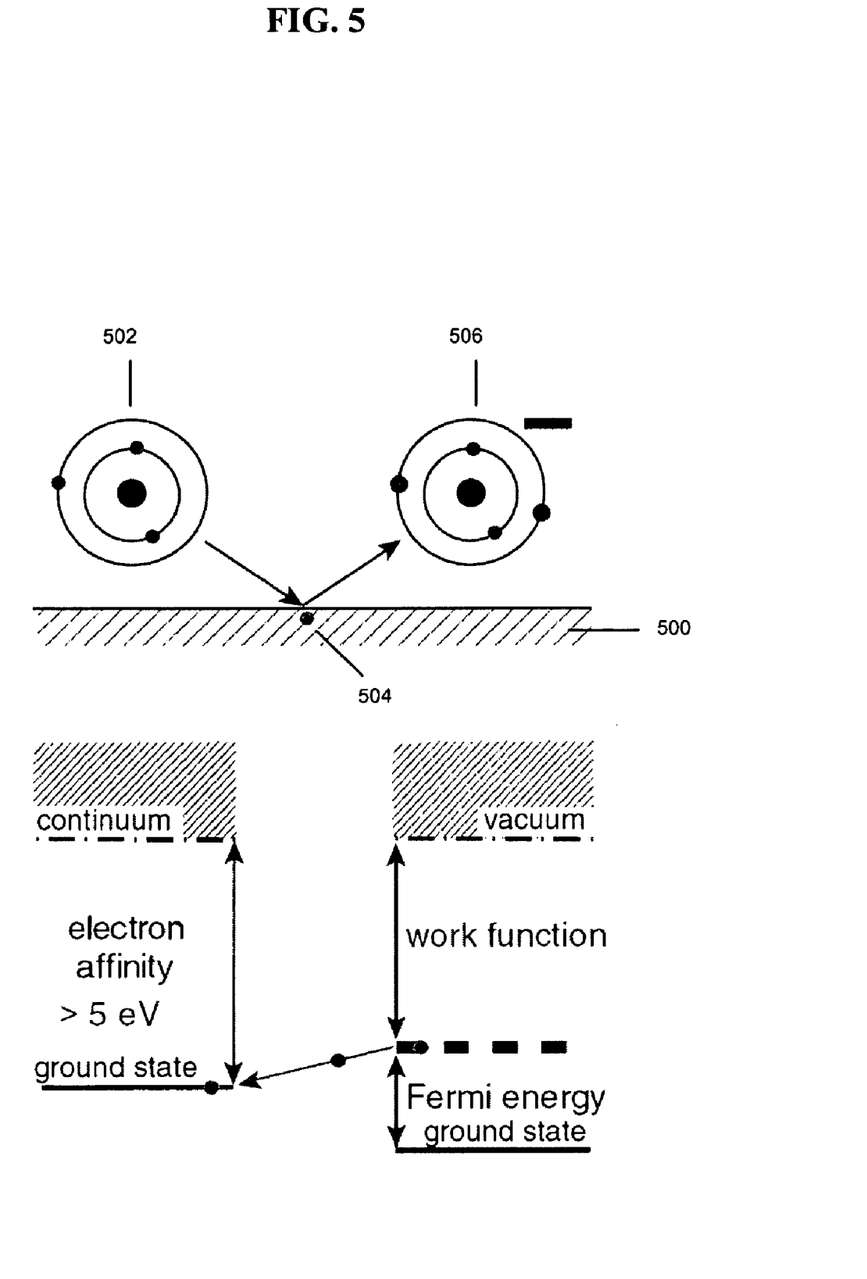
FIG. 5 is an illustration depicting the principle of negative surface ionization according to example embodiments.

For example, referring to FIG. 5, when approaching a relatively hot surface 500, an atom/molecule 502 may become polarized by the forces between its nucleus and the free electrons inside the relatively hot surface 500. The atom/molecule 502 may adhere to the relatively hot surface 500 under the action of these forces. If the work function (Φ) of the relatively hot surface 500 is smaller than the electron affinity (EA) of the absorbed atom/molecule 502, then an electron 504 at the Fermi level in the conduction band of the relatively hot surface 500 may shift by tunneling to the electron affinity level of the atom/molecule 502. Consequently, there may be a probability that the adsorbed atom/molecule 502 will transition from a neutral state to a negative ionic state. If the temperature of the relatively hot surface 500 is sufficiently high, then the adsorbed atom/molecule 502 may accumulate enough energy to overcome the binding forces so as to result in thermal desorption. During thermal desorption, the adsorbed atom/molecule 502 may be ejected as an ion 506 with relatively low energy from the relatively hot surface 500.

The likelihood of ionization may be described as a function of the surface temperature, the work function of the surface material, and the electron affinity of the atom/molecule to be ionized. The probability that a negative ion will be emitted may be mathematically expressed by a set of equations. For example, the equilibrium ratio (α) of ion flux ($N^-$) to neutral flux ($N^n$) leaving from the heated surface may be provided by the Saha-Langmuir (S-L) equation as shown by equation (4) below:

$$\alpha = \frac{N^-}{N^n} = \frac{g^-}{g^n} \exp\left[\frac{q(EA - \Phi)}{kT}\right] \quad (4)$$

wherein:
$N^-$=emission rate of negative ions
$N^n$=emission rate of neutral species
φ=work function of the surface [eV]
EA=electron affinity of atom or molecule [eV]
k=Boltzmann's constant ($8.617 \times 10^{-5}$ eV/K)
T=absolute surface temperature [K]
$g^-$,=statistical weighting factors for the negative ion and neutral $g^n$ atom/molecule, respectively. They are related to the total spin S of the respective species given by $$g = 2S + 1 = 2\sum_i s_i + 1,$$

wherein $s_i$ is the spin on the $i^{th}$ electron

The ionization efficiency (β) may be in equilibrium when the total number of particles ($N_0$) is equal the sum of $N^- + N^n$. The ionization efficiency (β) may be expressed by equation (5) below:

$$\beta = \frac{\alpha}{1+\alpha} = \frac{N^-}{N_0} = \frac{1}{1 + \frac{g^n}{g^-}\exp\left(\frac{q(\Phi - EA)}{kT}\right)} \quad (5)$$

wherein:
$N^-$=emission rate of negative ions
$N^n$=emission rate of neutral species
φ=work function of the surface [eV]
EA=electron affinity of atom or molecule [eV]
k=Boltzmann's constant ($8.617 \times 10^{-5}$ eV/K)
T=absolute surface temperature [K]
$g^-$,=statistical weighting factors for the negative ion and neutral $g^n$ atom/molecule, respectively. They are related to the total spin S of the respective species given by $$g = 2S + 1 = 2\sum_i s_i + 1,$$

wherein $s_i$ is the spin on the $i^{th}$ electron

In view of the above equations, it may be appreciated that higher temperatures may have higher ionization potential. Additionally, it may be appreciated from equation (6) below that the residence time (τ) of the impinging particle may be reduced with higher temperature.

$$\tau = \tau_0 \exp\left(\frac{E_{ads}}{kT}\right) \quad (6)$$

wherein:
$E_{ads}$=ion adsorption energy [eV]
$\tau_0$=vibrational period of the ion near the surface [s]
k=Boltzmann's constant ($8.617 \times 10^{-5}$ eV/K)
T=absolute surface temperature [K]

The ion adsorption energy ($E_{ads}$) may a few eV, and $\tau_0$ may be about $10^{-13}$ s. The ionization probability may be independent of the initial kinetic energy as long as the initial kinetic energy is smaller than or comparable to the adsorption energy, because the residence time (τ) on the heated surface may be sufficient to ensure thermal equilibrium with the heated surface.

A negative surface ion source apparatus according to example embodiments may include an evaporation unit, a vacuum system, an ionization unit, and an extraction unit. The extraction unit may include magnets for removing excess electrons. Ionization and extraction according to example embodiments may include transferring a $^{185/186}$Re mixture into a crucible and inserting the crucible into the evaporation unit. A vacuum may be established in the evaporation unit. The perrhenate molecules of the $^{185/186}$Re mixture may be evaporated under a vacuum. The perrhenate molecules then may be ionized in the ionization unit. The resulting perrhenate ions may be extracted from the ionization unit as a beam, wherein the beam may be shaped for injection into a mass separator to separate the $^{185}$Re from the $^{186}$Re.

A method of isolating $^{186}$Re according to example embodiments will be discussed in further detail below. An irradiated chemically-undefined $^{185/186}$Re mixture may be chemically converted into a perrhenate salt (different counter ions are suitable). The perrhenate salt may be dissolved in water and transferred to a vaporization crucible. The water may be completely evaporated from the crucible, such that the $^{185/186}$Re perrhenates may be adhered to the walls of the crucible.

The crucible may be made of a refractory material with a relatively low work function. For example, the crucible may be formed of tungsten (W), molybdenum (Mo), tantalum (Ta), or Lanthanum-Hexaboride, although example embodiments are not limited thereto. The cavity of the crucible may be comprised of a hollow cylinder with one side closed and the opening directly attached to the vaporization unit. The inner diameter and depth of the cavity may be in the mm to cm range and may be adjusted as needed.

The crucible may be disposed in a filament of the evaporation unit for ohmic heating. After the crucible with the perrhenate has been inserted into the filament of the evaporation unit, a vacuum may be established (e.g., about $10^{-5}$ to $10^{-7}$ Torr). The crucible may be heated to a temperature of about 1500° C.

After evaporation, the volatile perrhenates may drift into the ionization unit. The temperature of the ionization unit may be controlled separately. The ionizer may be made of a refractory material with a relatively low work function. The ionizer may have a tubular shape. The ionizer may also be filled with a porous material or a screen so as to enhance the ionizing process by increasing the surface area. The ionizer may be ohmically heated by a filament up to temperatures of about 1500° C. It may be beneficial for the transition connection between the evaporator and the ionizer to be relatively tight so as to reduce or prevent the loss of the volatile perrhenates. The transition connection may also provide thermal insulation between the evaporator and the ionizer to allow independent control of the evaporation and ionizing processes.

Upon operation of the ion source, a plasma including of an equilibrium of volatile ionized and neutral perrhenates may be generated in the ionizer volume. An excess of free electrons, formed during the ionization process, may also be present. To reduce or prevent further acceleration of the excess free electrons, a relatively weak magnetic field may be established at the "exit" of the ionizer to draw the excess free electrons towards the screening electrode.

The negatively ionized species may be accelerated from the ionizer by an electric field produced by a series of extraction electrodes having different voltage levels. The perrhenate ions and the excess free electrons may be initially accelerated from the ionizer region by the extraction electrode. The perrhenate ions may then be further accelerated and shaped by the screening electrode, whereas the excess free electrons (which have smaller mass) will hit the screening electrode and so be removed from the perrhenate ion beam. The final extracted perrhenate ion beam may be additionally shaped by magnetic and/or electrostatic beam optics and then injected into a mass separator to separate the $^{185}$Re from the $^{186}$Re.

Although the example embodiments detailed above are directed to the production of higher SA $^{186}$Re compounds, the present disclosure is not limited thereto. For instance, the methods and apparatuses described above may be applied to the extraction of other radioisotope species (e.g., $^{99}$Mo compounds) that can be vaporized and negatively charged within an ion source chamber constructed and operated in accord with the detailed description provided above. Accordingly, the methods and apparatuses according to example embodiments may be utilized to produce an increased volume of a range of higher SA radioisotope materials having a longer shelf life and improved therapeutic and/or diagnostic effects compared to conventional production and purification techniques.

While example embodiments have been disclosed herein, it should be understood that other variations may be possible. Such variations are not to be regarded as a departure from the spirit and scope of example embodiments of the present disclosure, and all such modifications as would be obvious to one skilled in the art are intended to be included within the scope of the following claims.

The invention claimed is:

1. A method of isolating a radioisotope to obtain a material with relatively high specific activity for production of a higher specific activity radiopharmaceutical, comprising:
    vaporizing a source compound containing a first isotope and a second isotope, the second isotope being a nuclear reaction product of the first isotope, the first isotope constituting a majority of the source compound, the second isotope being a radioisotope having a shorter half-life than the first isotope and having at least one of therapeutic and diagnostic properties when used as a radiopharmaceutical;
    ionizing the vaporized source compound to form charged atoms or molecules of the first isotope and the second isotope;
    separating the charged atoms or molecules to isolate the atoms or molecules of the second isotope; and
    collecting the isolated charged atoms or molecules of the second isotope with an oppositely-charged collector to obtain a material having a specific activity above 30 curies/mg.

2. The method of claim 1, wherein the source compound is vaporized in a vacuum.

3. The method of claim 1, wherein separating the charged atoms or molecules includes generating an electric field to extract and accelerate the charged atoms or molecules away from an ion source.

4. The method of claim 1, wherein separating the charged atoms or molecules includes generating a magnetic field to draw excess free electrons away from the charged atoms or molecules.

5. The method of claim 1, wherein separating the charged atoms or molecules includes injecting the charged atoms or molecules into a mass separator to isolate the atoms or molecules of the second isotope.

6. The method of claim 1, wherein the isolated charged atoms or molecules of the second are collected with a collector assembly.

7. The method of claim 6, wherein the collector assembly is water-cooled.

8. The method of claim 1, further comprising:
    producing the source compound with a (n,γ) or (γ,n) reaction.

9. The method of claim 1, wherein the first isotope is $^{98}$Mo or $^{100}$Mo.

10. The method of claim 1, wherein the second isotope is $^{99}$Mo.

11. A method of isolating $^{186}$Re to obtain a material with relatively high specific activity, comprising:
    vaporizing a source compound containing a primary Re isotope and $^{186}$Re, the $^{186}$Re being a nuclear reaction product of the primary Re isotope, the primary Re isotope constituting a majority of the source compound, the $^{186}$Re having a shorter half-life than the primary Re isotope;
    ionizing the vaporized source compound to form charged atoms or molecules of the primary Re isotope and $^{186}$Re;
    separating the charged atoms or molecules to isolate the atoms or molecules of $^{186}$Re; and
    collecting the isolated charged atoms or molecules of $^{186}$Re with an oppositely-charged collector to obtain a material having a specific activity above 30 curies/mg.

12. The method of claim 11, wherein the source compound is vaporized in a vacuum.

13. The method of claim 11, wherein the source compound is vaporized in an ion source at a temperature below about 1500° C. and a pressure below about 1 Torr.

14. The method of claim 11, wherein the vaporized source compound is ionized with hydrogen plasma.

15. The method of claim 11, wherein the vaporized source compound is ionized by impinging atoms or molecules of the vaporized source compound onto a heated surface, the work function of the heated surface being different from the electron affinity of the atoms or molecules, thus resulting in charged atoms or molecules being ejected from the heated surface.

16. The method of claim 11, wherein the source compound is ionized in an ion source at a temperature below about 1500° C. and a pressure below about 1 Torr.

17. The method of claim 11, wherein separating the charged atoms or molecules includes generating an electric field to extract and accelerate the charged atoms or molecules away from an ion source.

18. The method of claim 17, wherein the electric field is generated with extraction electrodes.

19. The method of claim 11, wherein separating the charged atoms or molecules includes generating a magnetic field to draw excess free electrons away from the charged atoms or molecules.

20. The method of claim 19, wherein the separating involves a screening electrode.

21. The method of claim 11, wherein separating the charged atoms or molecules includes injecting the charged atoms or molecules into a mass separator to isolate the atoms or molecules of $^{186}$Re.

22. The method of claim 11, wherein the isolated charged atoms or molecules of $^{186}$Re are collected with a collector assembly.

23. The method of claim 22, wherein the collector assembly is water-cooled.

24. The method of claim 11, wherein the primary Re isotope is $^{185}$Re or $^{187}$Re.

* * * * *